(12) United States Patent
Shibata et al.

(10) Patent No.: US 7,806,903 B2
(45) Date of Patent: Oct. 5, 2010

(54) CLIPPING INSTRUMENT FOR AN ENDOSCOPIC SURGICAL DEVICE

(75) Inventors: Hiroaki Shibata, Saitama (JP); Tomohiro Kawano, Tokyo (JP)

(73) Assignee: Hoya Corporation, Tokyo (JP)

( * ) Notice: Subject to any disclaimer, the term of this patent is extended or adjusted under 35 U.S.C. 154(b) by 333 days.

(21) Appl. No.: 12/131,316

(22) Filed: Jun. 2, 2008

(65) Prior Publication Data
US 2008/0312665 A1 Dec. 18, 2008

(30) Foreign Application Priority Data
Jun. 13, 2007 (JP) .............................. 2007-156288

(51) Int. Cl.
*A61B 17/10* (2006.01)
(52) U.S. Cl. ...................... 606/142; 600/104
(58) Field of Classification Search ................ 606/139, 606/142–143, 151, 157, 219; 600/104, 106–107; 227/175.1
See application file for complete search history.

(56) References Cited

U.S. PATENT DOCUMENTS

| | | | | |
|---|---|---|---|---|
| 5,520,701 | A | * | 5/1996 | Lerch ........................... 606/142 |
| 5,634,932 | A | * | 6/1997 | Schmidt ....................... 606/157 |
| 6,814,742 | B2 | | 11/2004 | Kimura et al. |
| 2001/0051812 | A1 | | 12/2001 | Ouchi |
| 2002/0177861 | A1 | | 11/2002 | Sugiyama et al. |
| 2003/0076412 | A1 | | 4/2003 | Ozawa |
| 2003/0179291 | A1 | | 9/2003 | Kobayashi et al. |
| 2007/0100205 | A1 | | 5/2007 | Iriyama |

FOREIGN PATENT DOCUMENTS

| | | |
|---|---|---|
| JP | 2002-191609 | 7/2002 |
| JP | 2006-87537 | 4/2006 |

OTHER PUBLICATIONS

English language Abstract of JP 2002-191609, Jul. 9, 2002, Kimura et al.
English language Abstract of JP 2006-87537, Apr. 6, 2006, Shibata.
U.S. Appl. No. 12/131,290 to Shibata et al., which was filed on Jun. 2, 2008.

* cited by examiner

*Primary Examiner*—Michael J Milano
*Assistant Examiner*—Victor X Nguyen
(74) *Attorney, Agent, or Firm*—Greenblum & Bernstein P.L.C.

(57) ABSTRACT

A clipping instrument for an endoscope is provided. The clipping instrument includes a flexible sheath, an operation wire, at least one detachable clip assembly, including a pair of clipping arms and a fastening ring. The clipping arms are configured to be projected forward to open outside the flexible sheath and to be closed to clip onto a treatment object outside the flexible sheath according to movements of the fastening ring. The clipping instrument further includes a sleeve formed to have a plurality of slits and a blade spring piece to be attached to the sleeve. The sleeve includes a plurality of blade springs, each of which is settled in one of the plurality of the slits of the sleeve when the blade spring piece is attached to the sleeve. The plurality of blade springs can resiliently hold the detachable clip assembly in a posture with respect to the flexible sheath.

6 Claims, 11 Drawing Sheets

CLIPPING INSTRUMENT FOR AN ENDOSCOPIC SURGICAL DEVICE

BACKGROUND OF THE INVENTION

The present invention relates to a surgical device having a clipping instrument to be inserted through a forceps channel of an endoscope.

Generally, in a clipping instrument for endoscopic surgeries, a clip having a pair of openable/closable arms and a fastening ring loosely fit around proximal portions of the arms is arranged in a distal end portion of a flexible sheath. The clip is configured such that the arms open and close as an operation wire, arranged in parallel with an axial direction of the flexible sheath, is advanced toward the distal end to push the fastening ring and retracted toward a proximal end to pull the fastening ring. The clip can be detached from the operation wire with its arms closed according to the operations to the operation wire. Such a configuration of the clipping instrument is disclosed in Japanese Patent Provisional Publication No. 2006-87537, for example.

When the clip of such conventional clipping instrument disclosed in the aforementioned publication is operated to be clipped onto in vivo tissue to indwell inside a body cavity, the arms are fully opened to their extent to be pressed onto the tissue and closed.

Therefore, the clipping instrument is provided a sleeve having a plurality (for example, three or four) of slits, which are parallel to an axial direction, at the distal end of the flexible sheath so that the fastening ring can resiliently outstretch the sleeve and penetrate therethrough, and the arms can be maintained open.

It is to be noted that after the fastening ring passed through the sleeve, the proximal portion of the clip remains inside the sleeve, and an outline of the remaining proximal portion is generally smaller than an outer diameter of the fastening ring. Therefore, the proximal portion may not be firmly held by the sleeve as the sleeve resiliently deforms, and the arms projecting out of the sleeve may be unstable and undesirably swayed. Thus, the clip may not be accurately handled to be pressed to a targeted portion of the body tissue.

SUMMARY OF THE INVENTION

In view of the foregoing drawback, the present invention is advantageous in that an endoscopic surgical device with a clipping instrument, in which the clipping arms can be steadily held open and operated in a stable posture, is provided.

According to an aspect of the present invention, there is provided a clipping instrument for an endoscope. The clipping instrument includes a flexible sheath to be inserted into an instrument channel of the endoscope, an operation wire, which is configured to be forwarded and retracted in an axial direction of the flexible sheath, at least one detachable clip assembly, including a pair of openable and closable clipping arms and a fastening ring to encircle proximal portions of the clipping arms, arranged in vicinity of a distal end portion of the flexible sheath with the clipping arms closed. The clipping arms are configured to be projected forward to open outside the flexible sheath and to be closed to clip onto a treatment object outside the flexible sheath according to forwarding and retracting movements of the fastening ring through the operation wire. The clipping instrument further includes a sleeve formed to have a plurality of slits and arranged at the distal end portion of the flexible sheath, and a blade spring piece to be attached to the sleeve. The blade spring piece has a plurality of blade springs, each of which is settled in one of the plurality of the slits of the sleeve when the blade spring piece is attached to the sleeve. The plurality of blade springs can resiliently hold the detachable clip assembly, being projected out of the flexible sheath, in a posture with respect to the flexible sheath.

DETAILED DESCRIPTION OF THE EMBODIMENT

Figure 1:
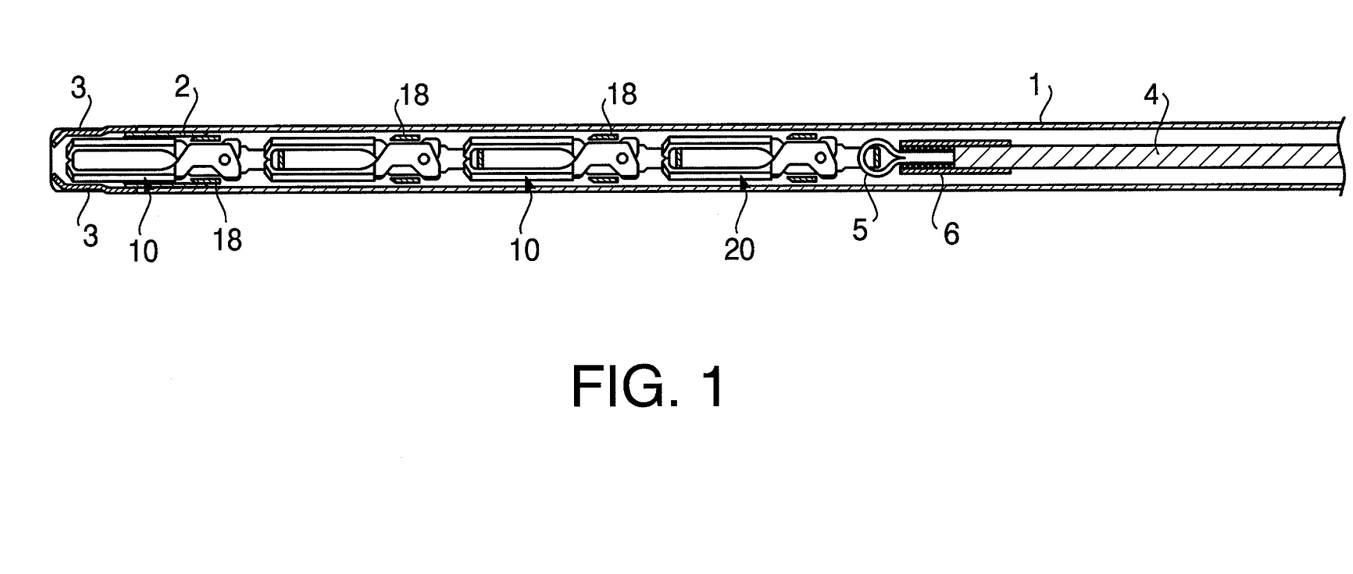
FIG. 1 is an overall cross-sectional side view of a clipping instrument with arms of a clip assembly being closed in a flexible sheath according to an embodiment of the present invention.
Figure 2:
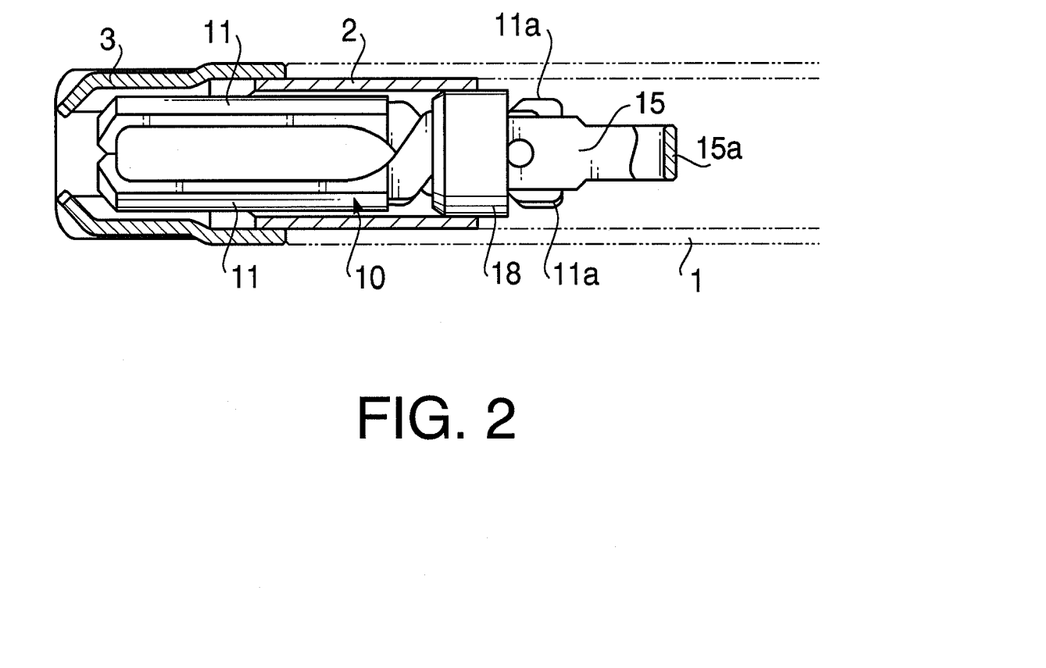
FIG. 2 is a partial and cross-sectional side view of the clip assembly being closed in the flexible sheath according to the embodiment of the present invention.

Hereinafter, referring to the accompanying drawings, an illustrative embodiment of the invention will be described. FIG. 1 is an overall cross-sectional side view of a clipping instrument 100 with arms 11 of a clip assembly 10 being closed in a flexible sheath 1 according to an embodiment of the present invention. FIG. 2 is a partial and cross-sectional side view of the clip assembly 10 being closed in the flexible sheath 1 according to the embodiment of the present invention.

The flexible sheath 1 is made of, for example, poly-tetra-fluoro-ethylene and is inserted into a forceps channel (not shown) of an endoscope (not shown).

The flexible sheath 1 is provided with a sleeve 2, which is made of a metal (e.g., stainless steel) at a distal end, and a blade spring piece 3 to prevent the clip assembly 10 from swaying is attached to the sleeve 2.

Inside the flexible sheath 1, an operating wire 4 to be advanced and retracted in parallel with the axial direction of the flexible sheath 1 is provided. The operating wire 4 is connected to an operating unit (not shown) at a proximal end thereof and can be advanced and retracted in accordance with an operation given to the operating unit. The operating wire 4 is fixedly connected to a connecting loop 5 through a connecting pipe 6.

Figure 3:
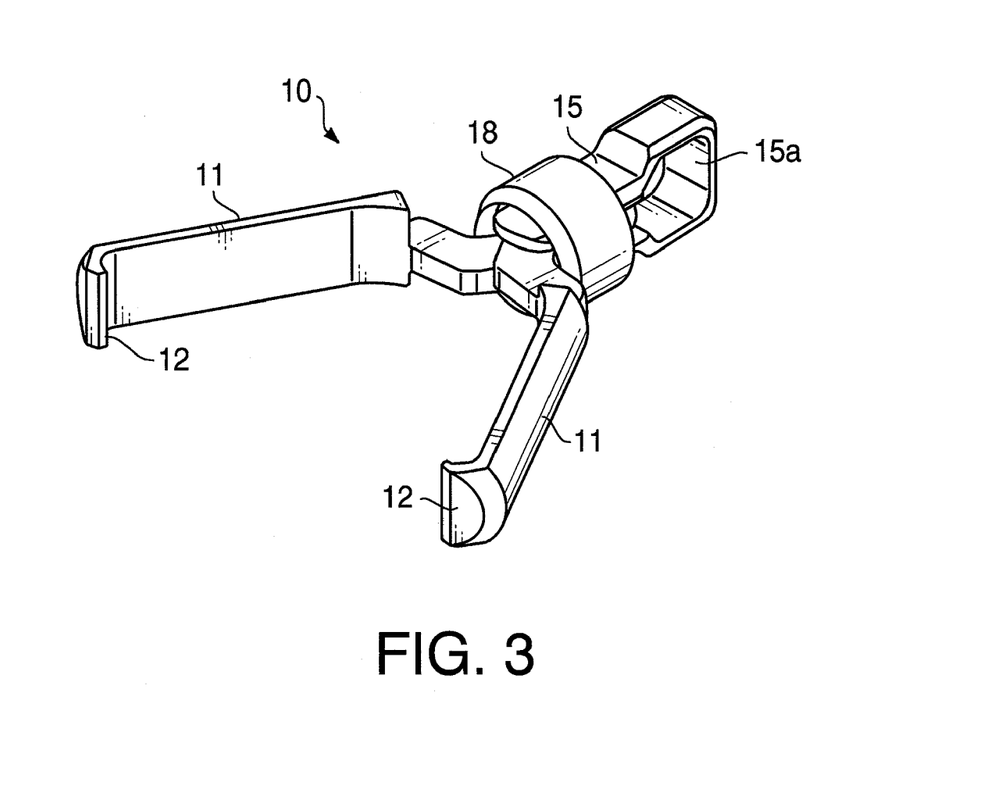
FIG. 3 is a perspective view of the clip assembly according to the embodiment of the present invention.
Figure 4:
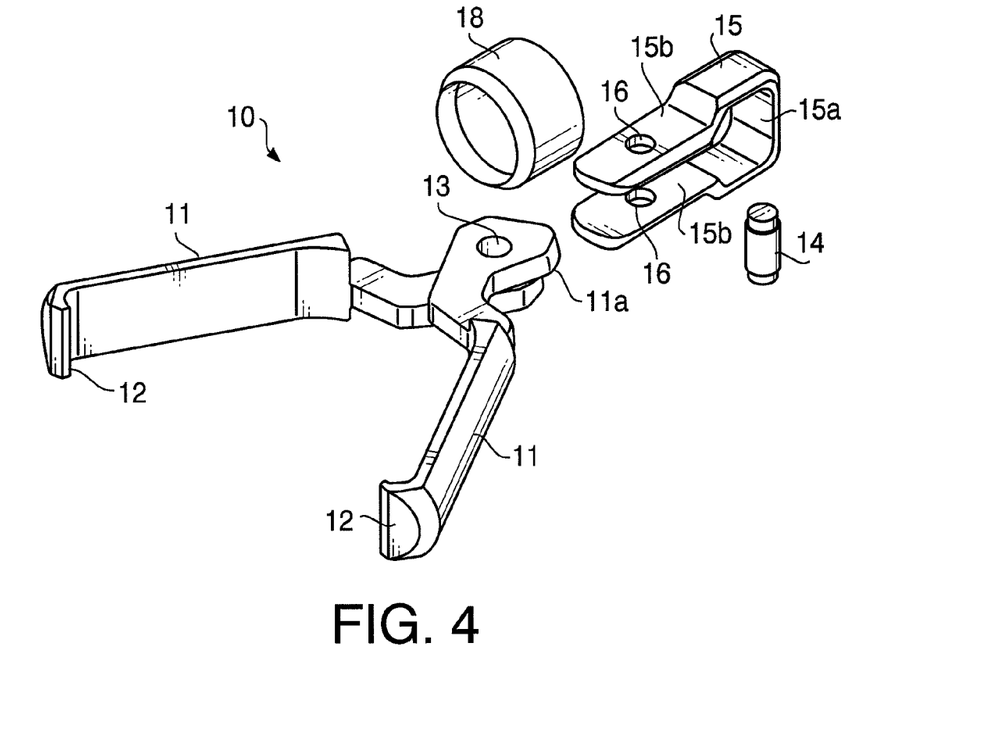
FIG. 4 is an exploded view of the clip assembly according to the embodiment of the present invention.

Further inside the flexible sheath 1, in vicinity to a distal end portion thereof, a plurality of clip assemblies 10 are aligned in line. FIG. 3 is a perspective view of one of the clip assemblies 10 according to the embodiment of the present invention. FIG. 4 is an exploded view of one of the clip assemblies 10 according to the embodiment of the present invention. The clip assembly 10 is provided with a pair of arms 11, each of which is individually formed and provided with a claw portion 12. The claw portion 12 is curved inward, when the arms 11 are assembled, so that the two claws 12 are opposed to each other to clutch a treatment object.

Each of the arms 11 is formed to have a through hole 13 in vicinity to a proximal end thereof. A shaft 14 supporting the arms 11 is penetrated through the through holes 13 of the arms 11 so that the arms 11, rotated about the shaft 14, can be arbitrarily opened and closed.

The clip assembly 10 is further provided with a tail portion 15, which includes an open-ringed connecting loop 15a at a proximal end thereof, a pair of plate portions 15b, which are parallel to each other and loosely nip the proximal end portion of the arms 11 therebetween, and through holes 16 through which the shaft 14 is penetrated. The tail portion 15 is connected to the operating wire 4 through another clip assembly 10 being aligned at a proximal side and a connecting clip 20, which will be described later.

Furthermore, the clip assembly 10 includes a fastening ring 18, by which the arms 11 are forcibly closed. When the arms 11 are allowed to be open, the fastening ring 18 is loosely fit around the proximal portion of the arms 11, as shown in FIG. 2.

When the fastening ring 18 is retracted rearward to an opening position shown in FIG. 3, in which the fastening ring 18 becomes in contact with cam portions 11a of the arms 11. Thus, the arms 11 are opened. In reverse, when the fastening ring 18 is forwarded, the arms 11 are forcibly closed.

Figure 5:
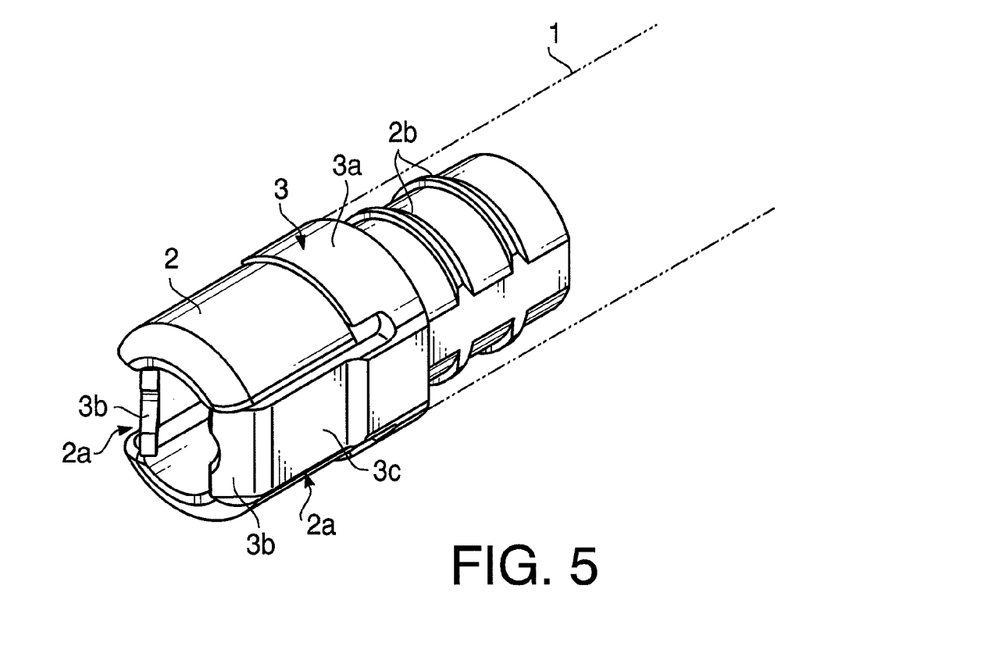
FIG. 5 is a perspective view of a sleeve and a blade spring piece in a distal end portion of the flexible sheath according to the embodiment of the present invention.
Figure 6:
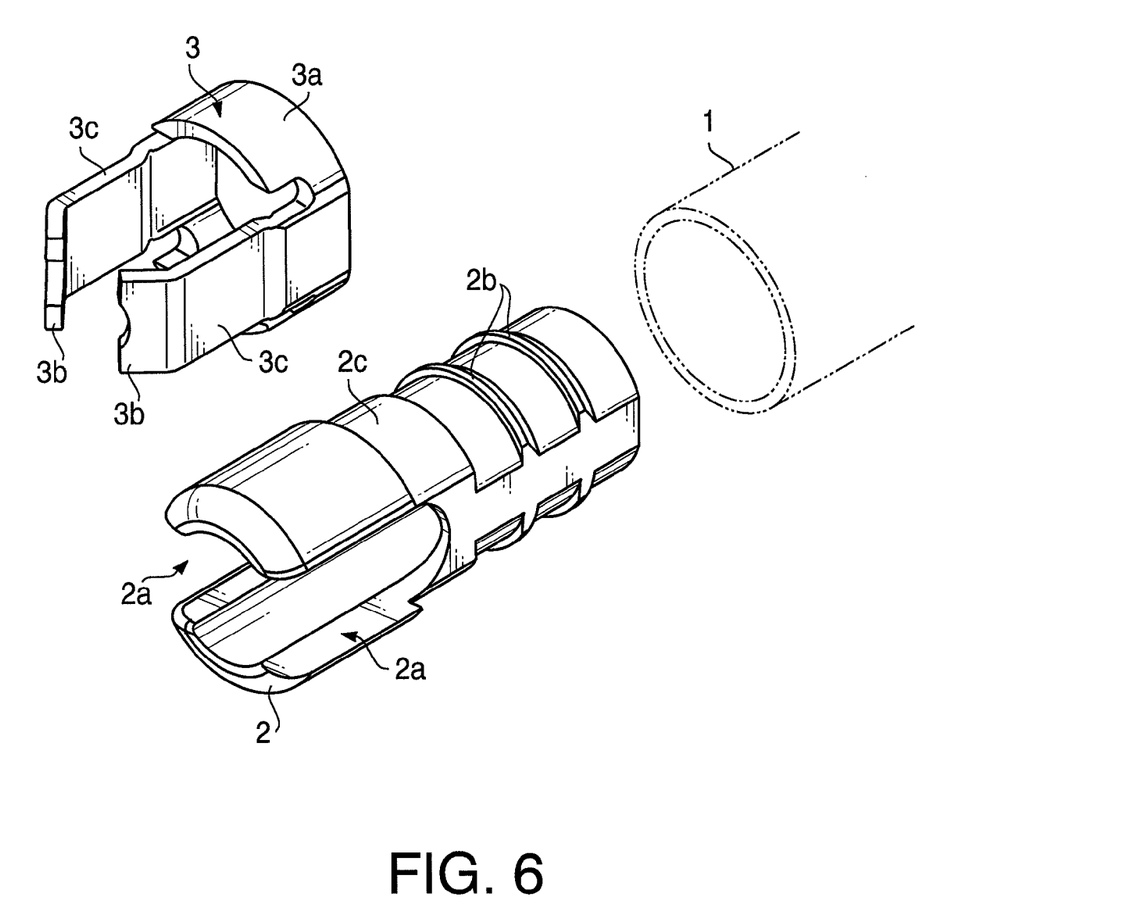
FIG. 6 is an exploded view of the sleeve and the blade spring piece in the distal end portion of the flexible sheath according to the embodiment of the present invention.

FIG. 5 is a perspective view of the sleeve 2 and the blade spring piece 3 in a distal end portion of the flexible sheath 1 according to the embodiment of the present invention. FIG. 6 is an exploded view of the sleeve 2 and the blade spring piece 3 in the distal end portion of the flexible sheath 1 according to the embodiment of the present invention. The sleeve 2 is formed to have slits 2a with substantial widths, which are in symmetric positions at 180 degrees from each other, at a distal half portion thereof. A proximal half portion of the sleeve 2 is formed to be substantially cylindrical and fixedly inserted into the flexible sheath 1. The proximal half portion includes stops 2b to be wedged into an inner surface of the flexible sheath 1 so that the sleeve 2 can be prevented from falling off from the flexible sheath 1.

In the present embodiment, the blade spring piece 3 includes two blade springs 3c and a ring portion 3a. The blade springs 3c are integrally coupled to the ring portion 3a, which is attached onto an outer surface of the sleeve 2 at a middle portion 2c. The sleeve 2 is formed to have an outer diameter of the middle portion 2c being substantially smaller than an outer diameter of the distal half portion so that the ring portion 3a can be fixedly fit into the middle portion 2c between the distal half portion of the sleeve 2 and the flexible sheath 1. Each of the blade springs 3c is settled in one of the slits 2a when the blade spring piece 3 is attached to the sleeve 2.

Figure 7:
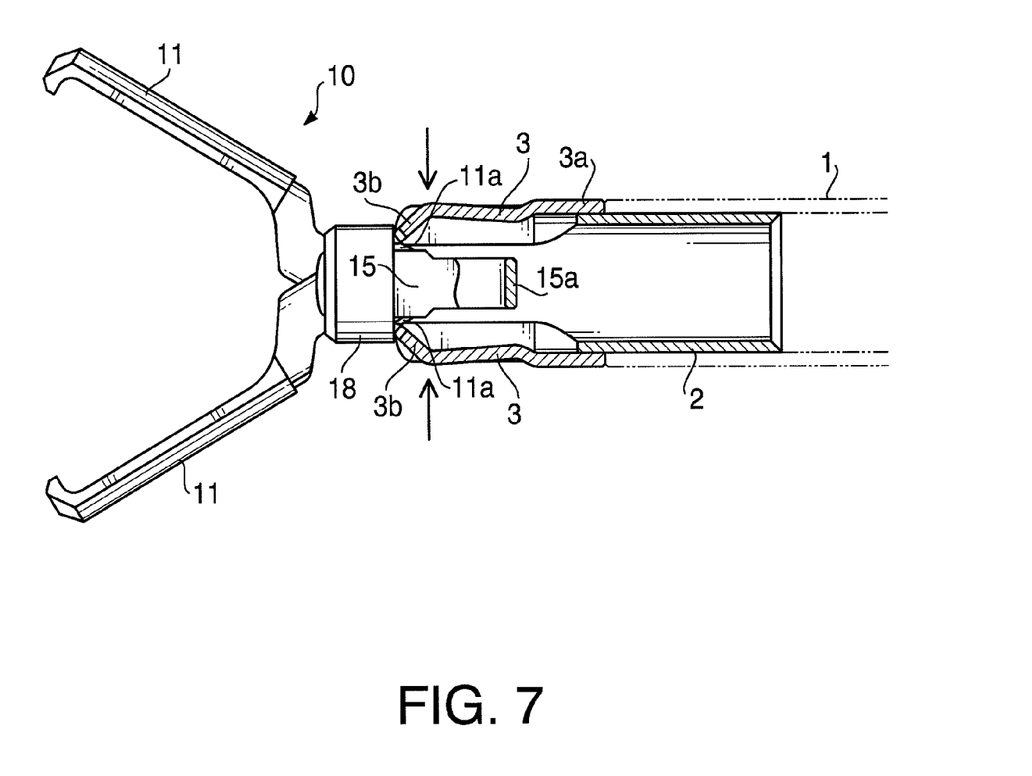
FIG. 7 is a side view of the clipping instrument with the arms of the clip assembly protruded outward according to the embodiment of the present invention.

The blade spring piece 3 further includes claw portions 3b, each of which is formed to extend from the blade spring 3c and obtusely angled inward. In addition, each of the claw portions 3b is formed to have an arc cutout to allow cam portions 11a of the clip assembly 10 to fit. A clearance between the two claw portions 3b are smaller than the inner diameter of the fastening ring 18 of the clip assembly 10; therefore, as shown in FIG. 7, the proximal portion of the clip assembly 10 is resiliently and steadily nipped by the claw portions 3b even after the fastening ring 18 passed through the claw portions 3b of the blade spring piece 3. FIG. 7 is a side view of the clipping instrument 100 with the arms 11 of the clip assembly 10 protruded outward according to the embodiment of the present invention.

Referring back to FIG. 1, in the flexible sheath 1 at the distal end portion, the clip assemblies 10 aligned in line are mutually connected. More specifically, the tail portion 15 of the clip assembly 10 in a position closer to the distal end of the flexible sheath 1 (front side) and the arms 11 of the clip assembly 10 in a position closer to the proximal end of the flexible sheath 1 (rear side) define a connected portion. The claws 12 of the arms 11 of the clip assembly 10 in the rear side are closed to clutch the connecting loop 15a of the clip assembly 10 positioned in the front side.

The clipping instrument 100 includes an undetachable clip assembly 20, which is undetachably connected to the connecting loop 5. Unlike the clip assemblies 10, the undetachable clip assembly 20 does not include the fastening ring 18; however, the remaining configuration of the detachable clip assembly 20 is identical to the clip assembly 10. The undetachable clip assembly 20 is connected to the tail portion 15 of the clip assembly 10 being located at the rear end of the aligned clip assemblies 10, i.e., the arms 11 of the undetachable clip assembly 20 are closed to clutch the tail portion 15 of the clip assembly 10 at the rear end.

The arms 11 of the plurality of mutually connected clip assemblies 10 and the undetachable clip assembly 20 are closed inside the flexible sheath 1 so that the clipping instrument 100 is inserted into the forceps channel of the endoscope.

Figure 8:
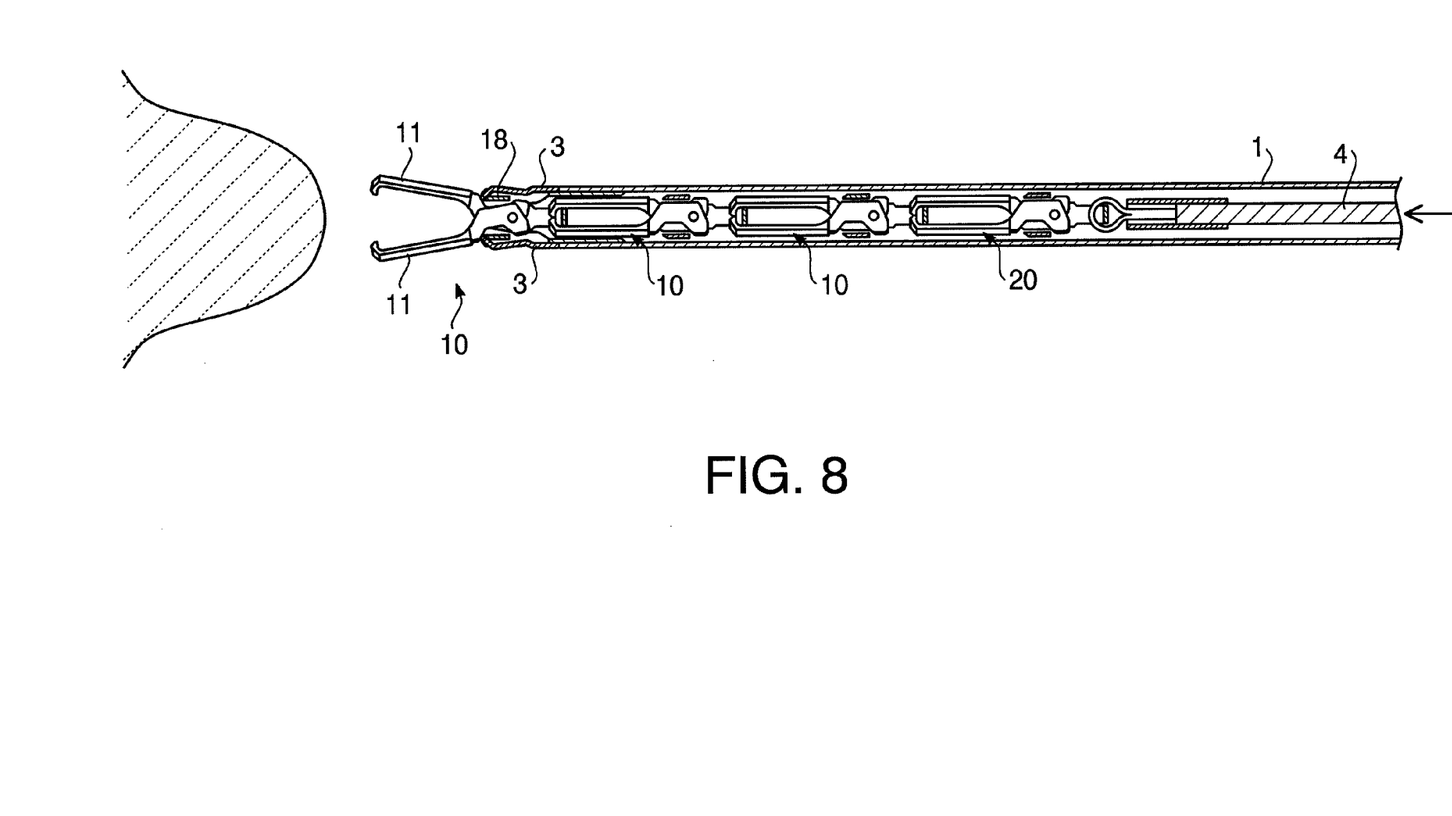
FIG. 8 is an overall cross-sectional side view of the clipping instrument with the clip assembly projecting out of the flexible sheath according to the embodiment of the present invention.
Figure 9:
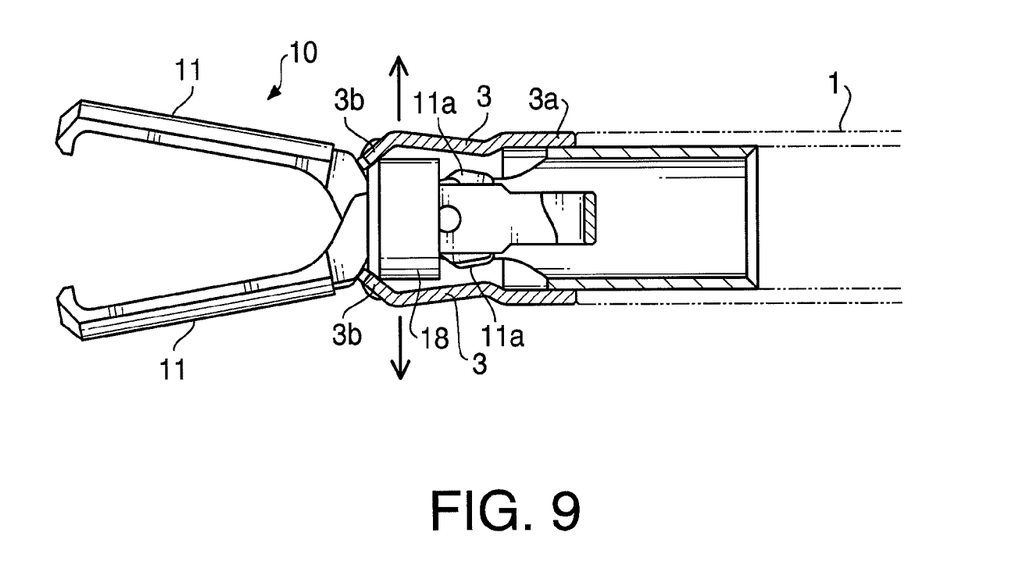
FIG. 9 is a cross-sectional side view of the clip assembly projecting out of the flexible sheath according to the embodiment of the present invention.
Figure 10:
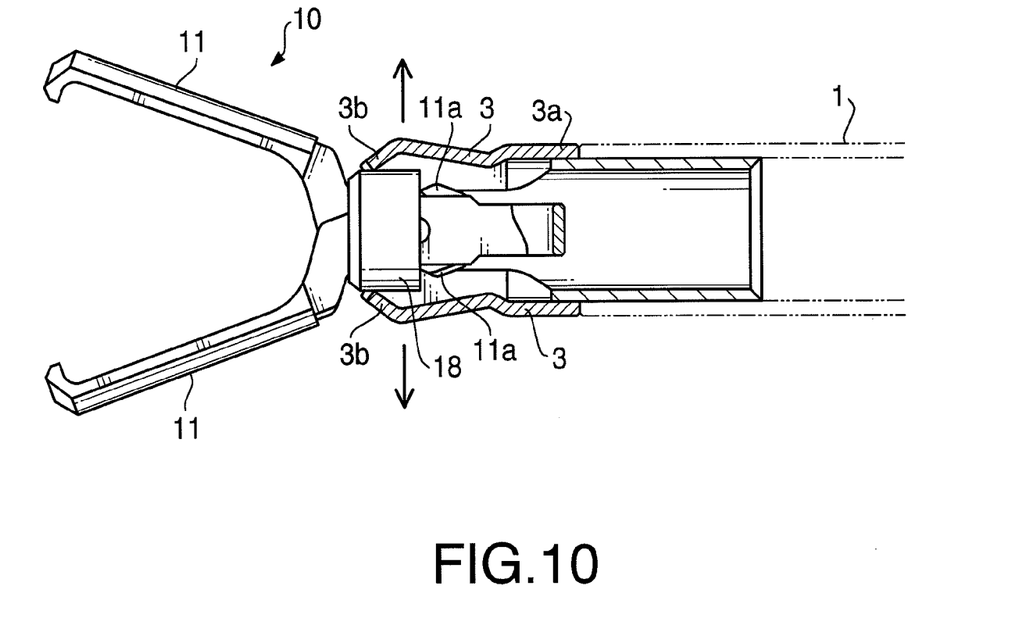
FIG. 10 is a cross-sectional side view of the clip assembly projecting further out of the flexible sheath according to the embodiment of the present invention.
Figure 11:
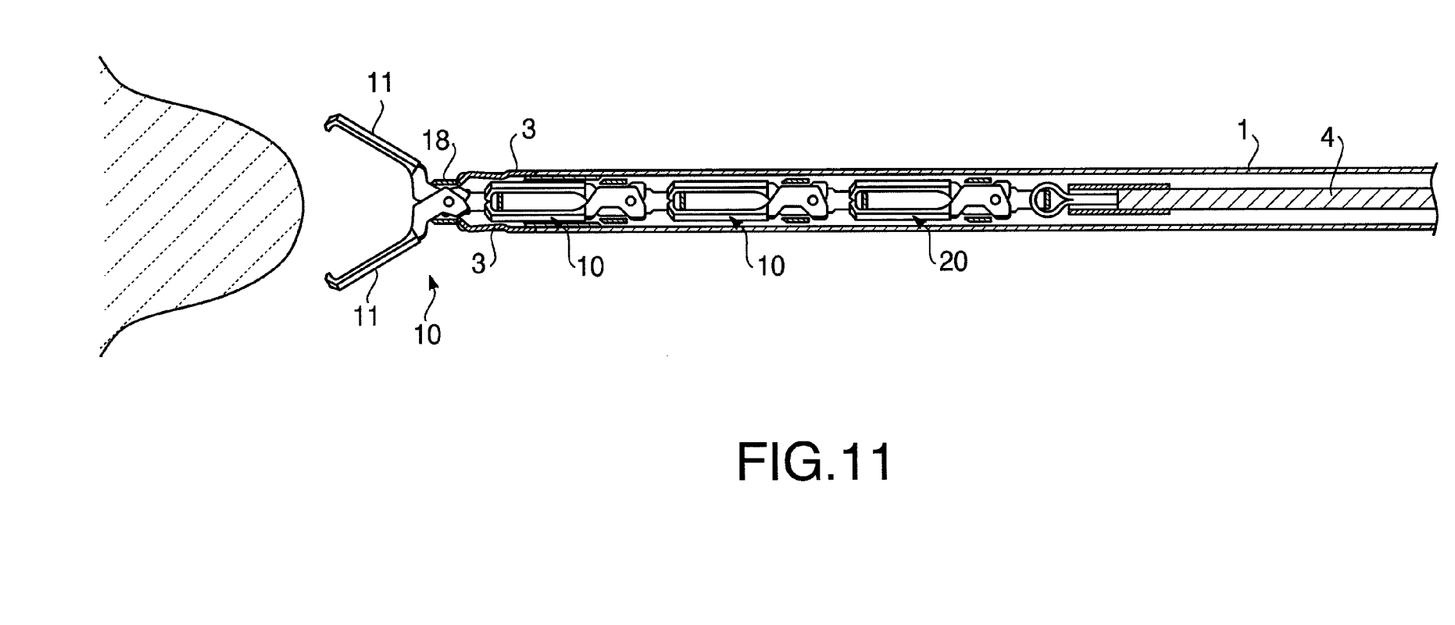
FIG. 11 is an overall cross-sectional side view of the clipping instrument with the arms open according to the embodiment of the present invention.
Figure 12:
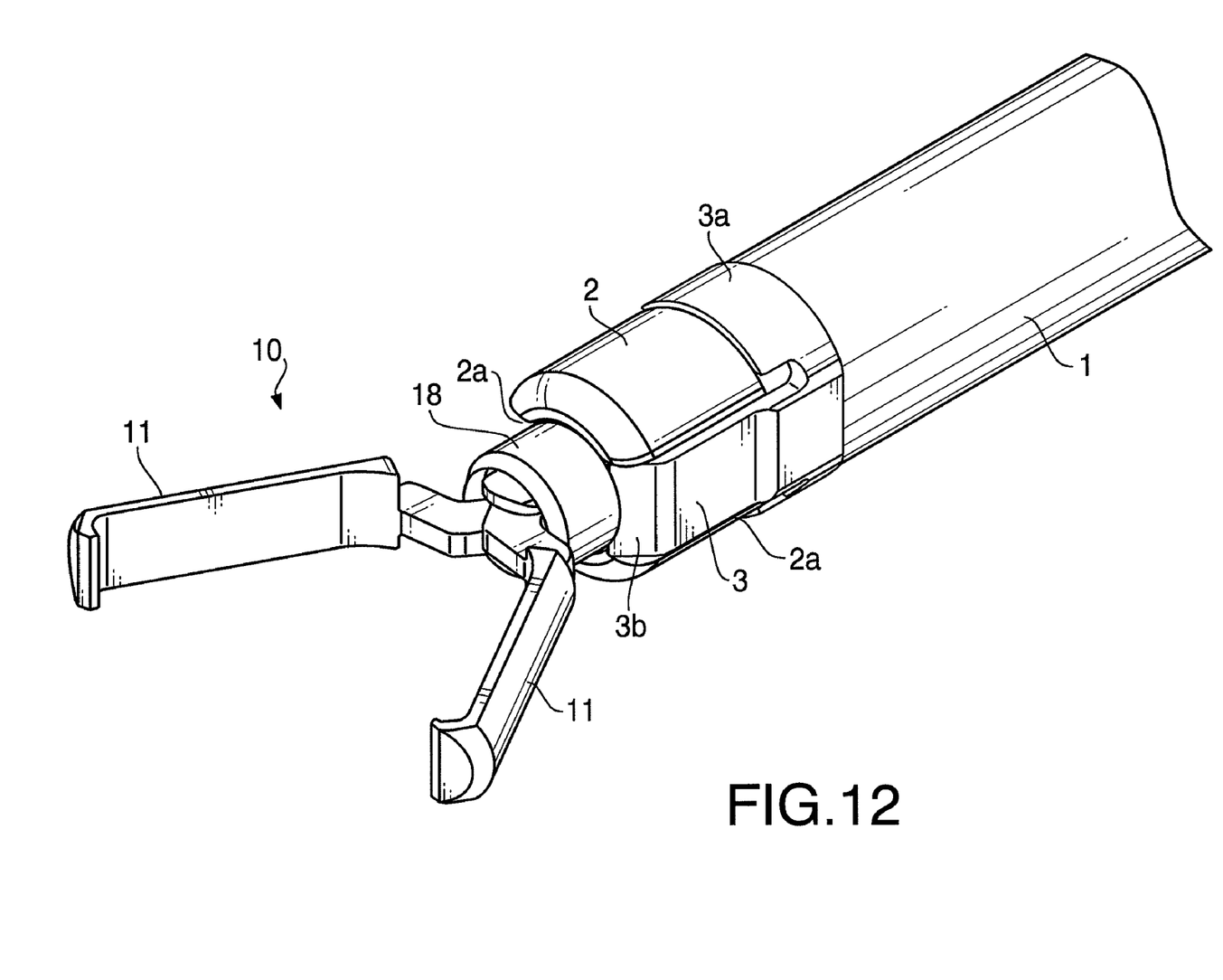
FIG. 12 is a perspective view of the clipping instrument with the arms of the clip assembly open according to the embodiment of the present invention.

Operations of the clipping instrument 100 configured as above in use in the forceps channel will be described with reference to FIGS. 1-2 and 8-14. FIGS. 8, 11, 13, and 14 are overall cross-sectional side views of the clipping instrument 100 in operation according to the embodiment of the present invention. FIGS. 9, 10 are cross-sectional side views of the clip assembly 10 projecting out of the flexible sheath 1 according to the embodiment of the present invention. FIG. 12 is a perspective view of the clipping instrument 100 with the arms 11 of the clip assembly 10 open according to the embodiment of the present invention.

When the flexible sheath 1 is inserted into the forceps channel of the endoscope, as shown in FIGS. 1 and 2, the clip assembly 10 at the front is entirely included in the flexible sheath 1. When the flexible sheath 1 in the forceps channel is brought in the vicinity of the treatment area, as shown in FIG. 8, the operation wire 4 is advanced from the proximal end so that the front clip assembly 10 is projected out of the flexible sheath 1 and the arms 11 are opened gradually.

Accordingly, as shown in FIG. 9, the arms 11, pushed forward, resiliently deforms and outstretches the blade springs 3c. The arms 11 are paused thereafter when the fastening ring 18 becomes in contact with the claw portions 3b due to resistance from the blade springs 3c.

When the clip assembly 10 is further advanced forward through the operation wire 4, as shown in FIG. 10, the fastening ring 18 is pushed forward to again resiliently deform and outstretch the blade springs 3c. Accordingly, as shown in FIG. 11, the fastening ring 18 is projected out of the flexible sheath 1.

FIGS. 7 and 12 illustrate the fastening ring 18 is entirely projected out of the flexible sheath 1 through the blade springs 3c. The arms 11 of the clip assembly 10 are fully opened by the fastening ring 18, and the claw portions 3b provides pressure to hold a portion adjoining the fastening ring 18 (i.e., the cam portions 11a) from the symmetric positions at 180 degrees.

According to the above configuration in which the blade springs 3c are provided separately from the sleeve 2, resiliency necessary and sufficient to hold the projected clip assembly 10 with the arms 11 open can be achieved. Thus, the arms 11 can be easily pressed onto the treatment area with accuracy.

Figure 13:
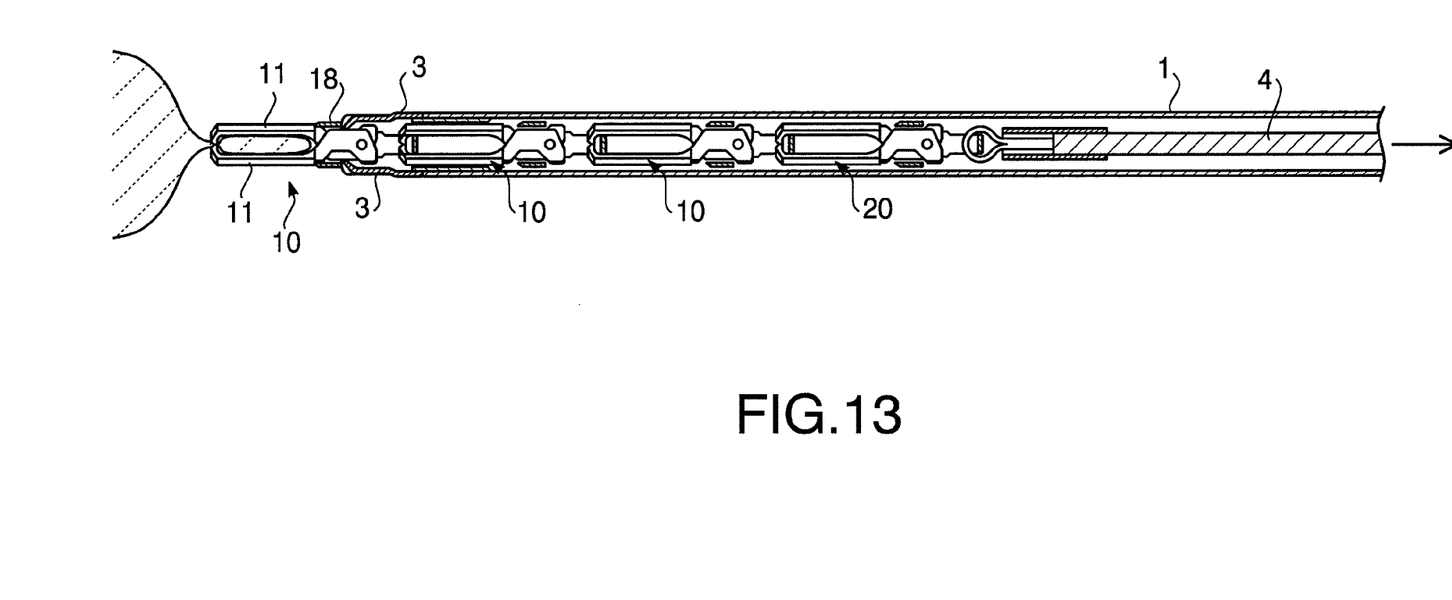
FIG. 13 is an overall cross-sectional side view of the clipping instrument with the arms closed according to the embodiment of the present invention.
Figure 14:
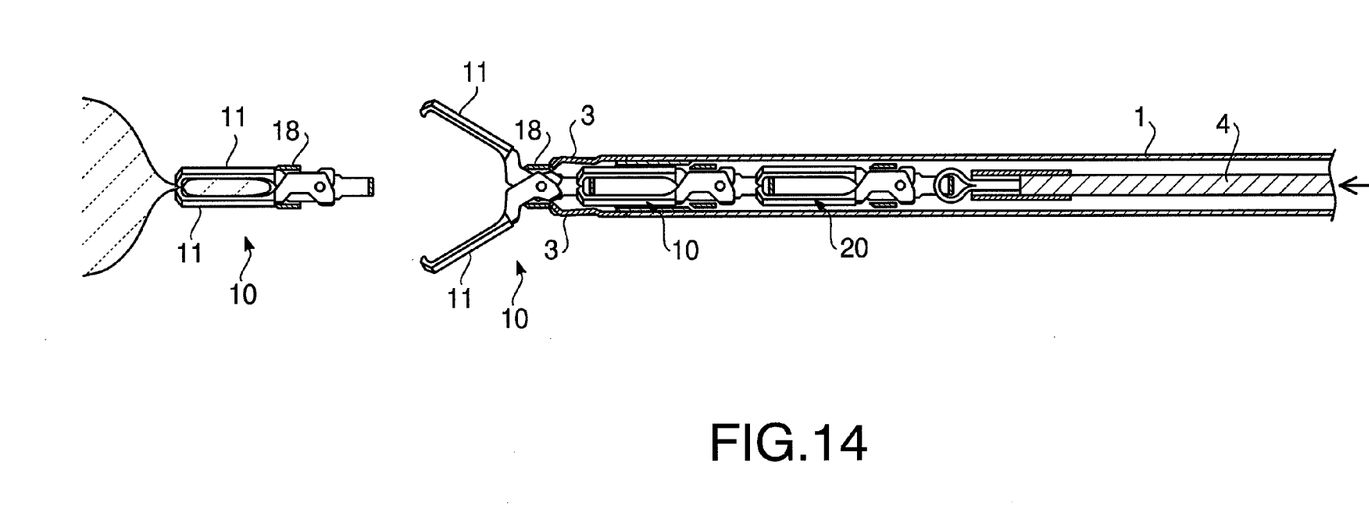
FIG. 14 is an overall cross-sectional side view of the clipping instrument with the clip assembly detached according to the embodiment of the present invention.

When the operation wire 4 is withdrawn to the proximal end, the arms 11 are forcibly closed by the fastening ring 18 to clutch onto the treatment area, as shown in FIG. 13. When the operation wire 4 is again advanced, as shown in FIG. 14, the arms 11 of the second clip assembly 10 become open, and the front clip assembly 10 is released from the connection. Thus, the front clip assembly 10 can remain clipping in the treatment area.

The above-described procedure can be repeatedly applied to the second and the following clip assemblies 10 as may be necessary.

Although an example of carrying out the invention has been described above, the present invention is not limited to the above described embodiments. For example, a single clip assembly 10 may be provided instead of two or more clip assemblies 10 in the clipping instrument 100. For another example, a number of the slits 2a and the blade springs 3c man not be necessarily two, but may be three or more. In such a configuration with three or more blade springs 3c, a form of the claw portions 3b is modified accordingly.

The present disclosure relates to the subject matter contained in Japanese Patent Application No. P2007-156288, filed on Jun. 13, 2007, which is expressly incorporated herein by reference in its entirety.

What is claimed is:

1. A clipping instrument for an endoscope, comprising:
   a flexible sheath to be inserted into an instrument channel of the endoscope;
   an operation wire, which is configured to be forwarded and retracted in an axial direction of the flexible sheath;
   at least one detachable clip assembly, including a pair of openable and closable clipping arms and a fastening ring to encircle proximal portions of the clipping arms, arranged in vicinity of a distal end portion of the flexible sheath with the clipping arms closed, the clipping arms being configured to be projected forward to open outside the flexible sheath and to be closed to clip onto a treatment object outside the flexible sheath according to forwarding and retracting movements of the fastening ring through the operation wire;
   a sleeve formed to have a plurality of slits and arranged at the distal end portion of the flexible sheath; and
   a blade spring piece to be attached to the sleeve, having a plurality of blade springs, each of which is settled in one of the plurality of slits of the sleeve when the blade spring piece is attached to the sleeve,
   wherein the plurality of blade springs can resiliently hold the detachable clip assembly, being projected out of the flexible sheath, in a posture with respect to the flexible sheath.

2. The clipping instrument according to claim 1,
   wherein the clip assembly projected out of the flexible sheath is nipped by inwardly angled portions of the blade springs to be held at a portion adjoining the fastening ring.

3. The clipping instrument according to claim 2,
   wherein each of the blade springs is formed to have a cutout for the portion of the clip assembly adjoining the fastening ring to fit.

4. The clipping instrument according to claim 1,
   wherein the blade spring piece includes a ring portion, which is integrally coupled with the plurality of blade springs and attached onto an outer surface of the sleeve.

5. The clipping instrument according to claim 4,
   wherein the sleeve includes a smaller-diameter portion, of which outer diameter is smaller than an outer diameter of a distal portion of the sleeve in which the plurality of slits are provided; and
   wherein the blade spring piece is fixedly fit in the smaller-diameter portion between the distal portion and the flexible sheath.

6. The clipping instrument according to claim 1,
   wherein a number of the slits formed in the sleeve corresponds to a number of the blade springs provided to the blade spring piece; and
   wherein each of the blade springs is settled in one of the slits when the blade spring piece is attached to the sleeve.

* * * * *